US00PP24834P3

(12) United States Plant Patent
Cummins et al.

(10) Patent No.: US PP24,834 P3
(45) Date of Patent: Sep. 2, 2014

(54) APPLE TREE ROOTSTOCK NAMED 'G.222'

(50) Latin Name: ***Malus domestica*×*Malus robusta* hybrid**
Varietal Denomination: G.222

(75) Inventors: James Cummins, Geneva, NY (US); Herbert Sanders Aldwinckle, Geneva, NY (US); Terence Lee Robinson, Geneva, NY (US); Gennaro Fazio, Geneva, NY (US)

(73) Assignee: Cornell University, Ithaca, NY (US)

( * ) Notice: Subject to any disclaimer, the term of this patent is extended or adjusted under 35 U.S.C. 154(b) by 152 days.

(21) Appl. No.: 13/506,243

(22) Filed: Apr. 6, 2012

(65) Prior Publication Data

US 2013/0269070 P1 Oct. 10, 2013

(51) Int. Cl.
*A01H 5/00* (2006.01)

(52) U.S. Cl.
USPC ..... Plt./174

(58) Field of Classification Search
USPC ..... Plt./174
See application file for complete search history.

(56) References Cited

PUBLICATIONS

Lehnert, Richart. "Mixup delays rootstock production." Good Fruit Grower. Jan. 15, 2012.*

"Apple Rootstock Geneva(R) 'G.222'," Retrieved from web on Feb. 10, 2013, <http://www.cornell.flintbox.com/public/project/21272/, pp. 1-2.

"Geneva Apple Rootstocks Comparison Chart," Retrieved from web on Feb. 10, 2013, <http://www.cctec.cornell.edu/plants/GENEVA-Apple-Rootstocks-Comparison-Chart-120911.pdf>, pp. 1-3.

* cited by examiner

*Primary Examiner* — Wendy C Haas

(74) *Attorney, Agent, or Firm* — MacMillan, Sobanski & Todd, LLC

(57) ABSTRACT

The present invention relates to a new and distinct variety of apple tree rootstock named 'G.222'. The 'G.222' apple tree rootstock is 45 to 55 percent of the size of a standard self-rooted seedling tree, induces precocity to the scion, encourages high yield efficiency, is resistant to fire blight and woolly apple aphid, is resistant to crown and root rots caused by *Phytophthora cactorum*, and is tolerant to replant disease complex.

5 Drawing Sheets

STATEMENT REGARDING FEDERAL FUNDING

This invention was made with United States government support under a United States Department of Agriculture—Agricultural Research Station Cooperative Research and Development Agreement, Sponsor's Contract Number 58-3K95-M-1031. The government has certain rights in the invention.

Genus and species: *Malus domestica*×*Malus robusta* hybrid.

Variety denomination: 'G.222'.

BACKGROUND AND SUMMARY OF THE INVENTION

I. Field & Utility Summary

The present invention relates to a new and distinct variety of apple tree. The apple tree is particularly useful in that it can be propagated clonally and used as a rootstock or root system for apple trees as well as for interstems of apple trees. The new variety is a dwarfing rootstock that is resistant to fire blight and crown rot. It is precocious and highly productive, and can be used as a rootstock and for interstems of apple trees.

II. Cultivation Summary

'G.222' originated from a planned cross in 1975 in Geneva, N.Y.

III. Comparisons

The seed parent *Malus domestica* 'Malling 27' is a super-dwarfing rootstock, i.e., trees grown on this rootstock are 15 to 20 percent the size of a standard self-rooted seedling tree. 'Malling 27' is known to induce good precocity to the scion (i.e., the ability to induce early reproductive development in the scion) and has high yield efficiency. 'Malling 27' may induce small fruit size in some scion cultivars. 'Malling 27' plants produce no spines, are poorly anchored, and are very sensitive to drought and winter cold. They are also susceptible to the woolly apple aphid (*Eriosoma lanigerum*) and to fire blight (*Erwinia amylovora*).

The pollen parent *Malus robusta* 'Robusta 5' is a non-dwarfing rootstock, i.e. trees on this rootstock are the same size as a standard self-rooted tree. 'Robusta 5' does not induce precocity to the scion and is not highly yield efficient. Juvenile plants of 'Robusta 5' produce many spines. 'Robusta 5' breaks buds very early in the spring and is winter hardy. It is resistant to powdery mildew (*Podosphaera leucotricha*) and fire blight, and is immune to the woolly apple aphid. Further, 'Robusta 5' has shown tolerance to the specific replant disease complex.

The 'G.222' apple rootstock of the present invention has a combination of qualities that distinguishes it from its parental plants (i.e., 'Malling 27' and 'Robusta 5'). For example, although 'G.222' has dwarfing properties derived from 'Malling 27', it is different from its dwarfing parent (i.e., 'Malling 27') because it produces a tree that is 45 to 55 percent of the size of a standard self-rooted seedling tree. Thus 'G.222' belongs to a different dwarfing vigor class than its 'Malling 27' parent. In particular, 'G.222' has dwarfing characteristics that are similar to the industry standard of *Malus domestica* 'Malling 26'. 'G.222' shares similarities with 'Malling 27' in that they both induce precocity to the scion and are highly yield efficient.

With regard to its 'Robusta 5' parent, 'G.222' is distinguishable in that it is a dwarfing rootstock and is highly yield efficient, while 'Robusta 5' is not. However, like 'Robusta 5', 'G.222' is resistant to fire blight and the woolly apple aphid (*Eriosoma lanigerum*). In addition, 'G.222' has been shown to have some tolerance to the replant disease complex.

As discussed above, 'G.222' is most similar to 'Malling 26' in terms of dwarfing class. However, 'G.222' is more precocious and yield efficient than 'Malling 26'. 'G.222' is resistant to fire blight whereas 'Malling 26' and other rootstocks in its market class are not.

IV. Breeding History

In the spring of 1975, pollen from a *Malus robusta* 'Robusta 5' apple tree was applied to emasculated flowers of a *Malus domestica* 'Malling 27' apple tree in Geneva, N.Y. In the fall of 1975, approximately 500 seeds resulting from this pollination were extracted from mature fruit derived from this cross. In the winter of 1975-76, the seeds were stratified and planted in large flats under conditions effective to germinate seeds and obtain seedlings. When germinated seedlings were about 2.5 cm tall they were inoculated with a mixture of isolates of the oomycete *Phytophthora cactorum* (the causal agent of crown and root rots). The flats were flooded to mid-hypocotyl level and kept at 23° C. for one week. Surviving seedlings were transplanted into individual pots.

In the summer of 1976, each of the transplanted seedlings was inoculated with approximately $10^6$ colony forming units of the Ea 273 strain of the fire blight bacterium *Erwinia amylovora* by inserting a 26-gauge hypodermic syringe needle into the shoot tip. The seedling designated as #222 was one of the 45 survivors of this battery of inoculations from the same cross. All the 45 surviving plants were transplanted to the Loomis field (Geneva, N.Y.) in the fall of 1976 and allowed to grow side shoots for propagation/evaluation. In 1979, 'G.222' was evaluated for rooting ability, lack of spine production, and low root brittleness in a layering bed (stool bed). In 1982, 4 finished trees with 'G.222' rootstock were planted in a first test orchard on the Loomis farm (Geneva, N.Y.) with *Malus domestica* cv. 'Northern Spy' grafted onto this rootstock as the scion cultivar. In addition in 1983 and 1984, one and four additional finished trees with *Malus domestica* cv. 'Northern Spy' as the scion were planted in evaluation orchards. This rootstock performed well (top 20% of many rootstocks tested) in these first test trials and during 1990-1993 more material was propagated by stool bed and nursery to be entered into new trials at the Hansen Farm (Geneva, N.Y.) with *Malus domestica* cv. Empire and Liberty as the scion cultivars. The 'G.222' rootstock performed well with all the scion cultivars that were tested, having matched or exceeded the yield efficiency, productivity and precocity of commercial controls. In August of 2002, several rootstock liners of 'G.222' were budded with 15 different scion cultivars to test graft union compatibility—the test results showed that 'G.222' was compatible with all the cultivars tested. Visual observations made on stool beds in the Loomis Farm and harvested liners in years 2002 through 2011 showed the absence of natural wooly apple aphid infestations, while present in neighboring susceptible plants, indicating that 'G.222' is resistant to infestations of the wooly apple aphid.

V. Asexual Reproduction

Asexual reproduction of the 'G.222' apple rootstock has been achieved using the traditional method of clonally propagating apple rootstocks. In particular, the original seedling of the 'G.222' apple rootstock was planted in the Loomis field (Geneva, N.Y.) and allowed to develop into a "mother plant." The 'G.222' mother plant was then used to obtain rooted liners using conventional layering procedures. The resulting liners were then planted in a row to generate a layering stool bed (also referred to as the "mother stool bed"). The living tissues (i.e. leaves, stems, roots, buds, and spines) of the mother stool bed were observed to be identical to secondary and tertiary stool bed plants. In addition to conventional layering, the 'G.222' apple rootstock variety has been asexually reproduced by root cuttings, by budding and grafting onto seedling and clonal rootstocks, and by tissue culture. Asexual reproduction by layering, root cuttings, budding, grafting and tissue culture in Geneva, N.Y. has shown that the claimed plant reproduces true to type through successive generations of asexual reproduction.

VI. Stability

Observations of trees from these propagations indicate that all trees have proven true to type and identical in all appearances to the original tree.

SUMMARY OF THE INVENTION

The present invention relates to a new and distinct variety of apple tree rootstock named 'G.222'. The 'G.222' apple tree rootstock is 45 to 55 percent of the size of a standard self-rooted seedling tree, induces precocity to the scion, encourages high yield efficiency, is resistant to fire blight and woolly apple aphid, is resistant to crown and root rots caused by *Phytophthora cactorum*, and is tolerant to replant disease complex.

DETAILED BOTANICAL DESCRIPTION OF THE INVENTION

Figure 1:
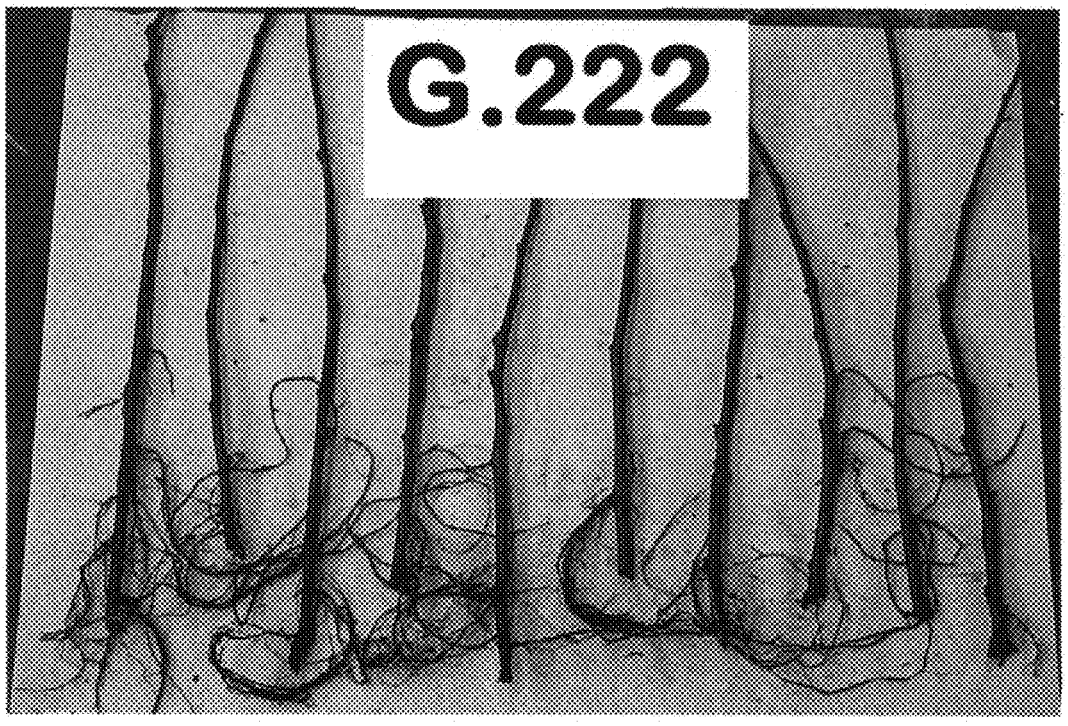
FIG. 1 shows a dormant shoot (including buds and bark).
Figure 2:
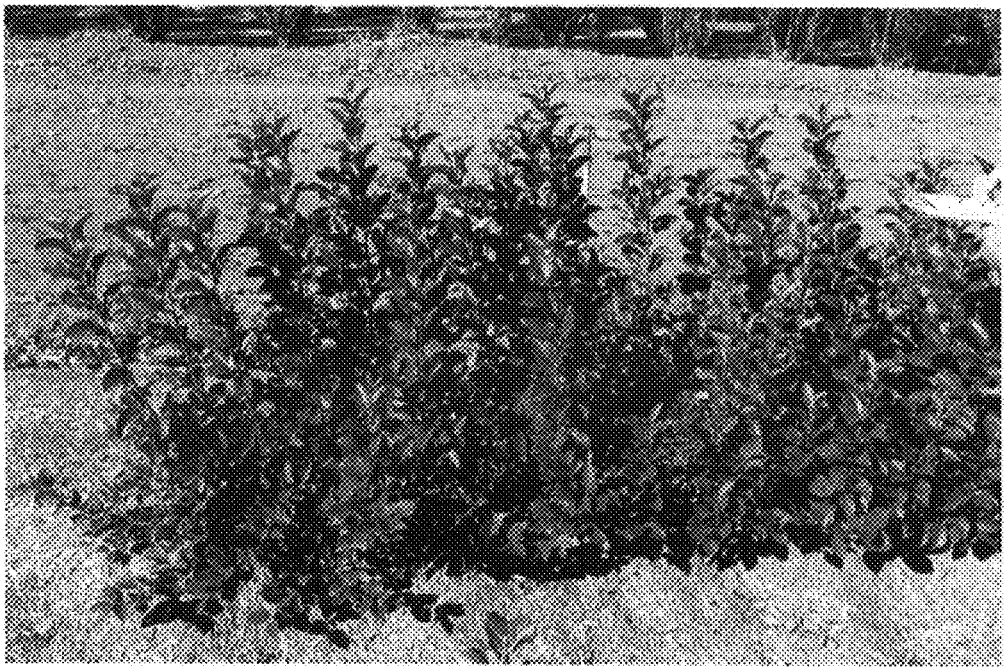
FIG. 2 shows actively growing shoots in a stool bed in Washington State.
Figure 3:
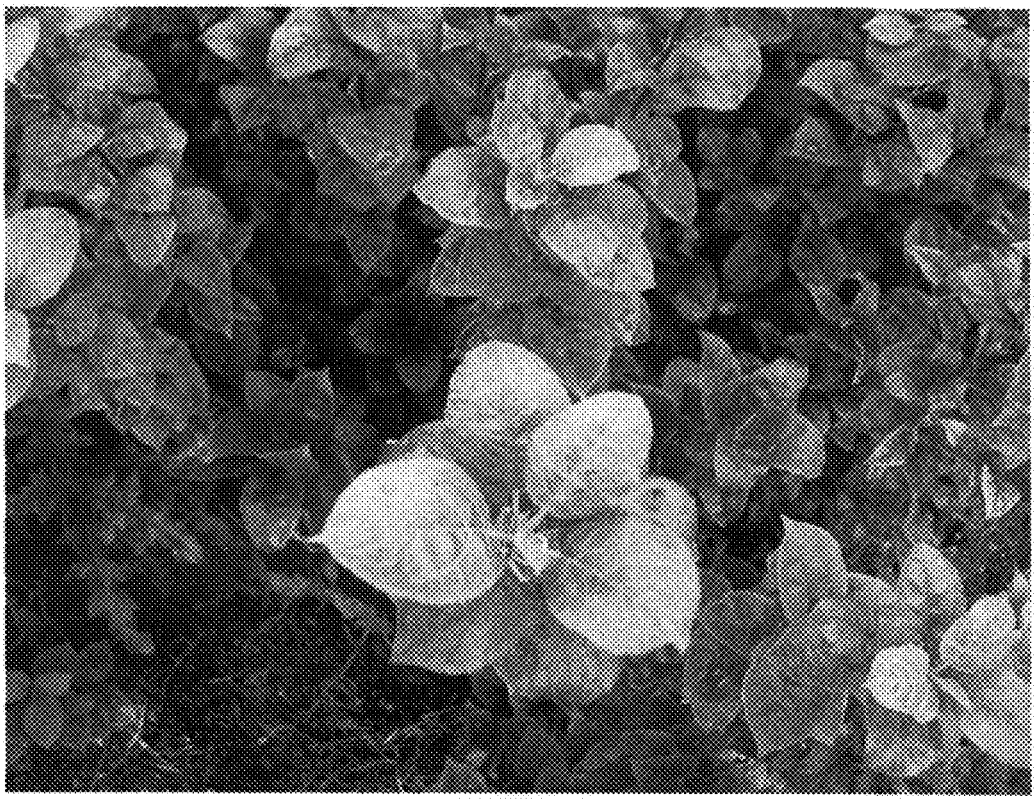
FIG. 3 shows the adaxial (upper) lamina surface of leaves on shoot apex.
Figure 4:
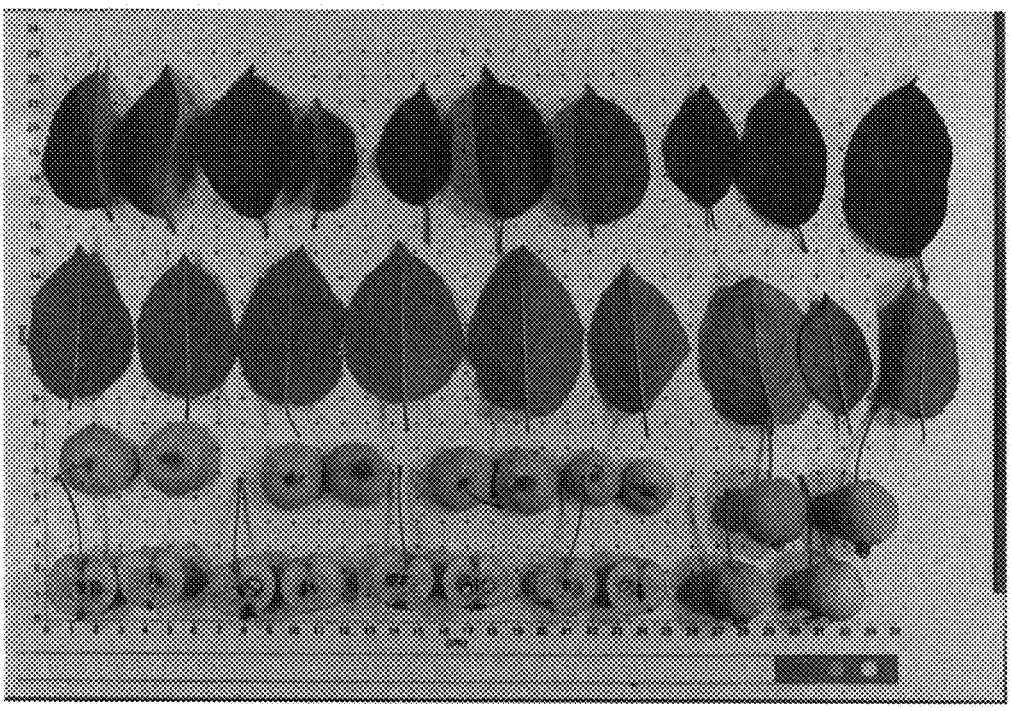
FIG. 4 shows leaves and mature fruit.
Figure 5:
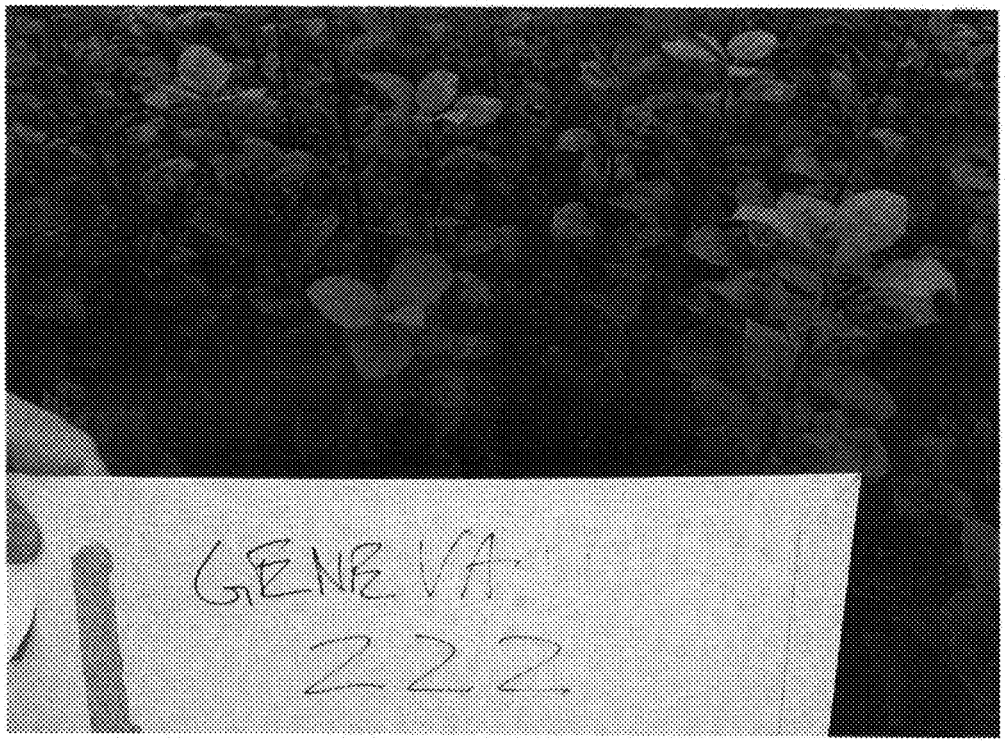
FIG. 5 shows actively growing stool bed in Geneva, N.Y.

The following description of apple tree rootstock 'G.222' contains references to color names taken from The Royal Horticultural Society Colour Chart (R.H.S.), 2001 edition. Botanical descriptions follow the Manual of Cultivated Plants (Bailey, 1949).

Tree:

*Habit*.—A self-rooted tree of 'G.222' is a small shrub typically standing about 1.5-2 meters tall by about 2 meters wide when 7 years old. There is no single dominant trunk. Instead there are few shoots arising from the crown. Very few suckers (i.e., new shoots emerging from below ground) are produced. Liners planted in the nursery stop apical growth mid season. The apical bud in these plants is pubescent Greyed-Green (RHS 191D).

*Productivity*.—In an intermediate trial performed in Geneva, N.Y., the 'G.222' rootstock received the cultivar 'Empire' (*Malus domestica*) as the scion and was compared to the *Malus domestica* check rootstocks M.9 EMLA, M.26 and M.7. 'G.222' was shown to have statistically higher ($p \leq 0.05$) yield efficiency (kg yield/$cm^2$ trunk cross sectional area) than all the check rootstocks.

*Precocity*.—Scion cultivars budded on 'G.222' exhibit similar precocity as those budded on M.9.

*Fertility* (*fecundity*).—The 'G.222' plant produces flowers and fruits regularly.

Dormant shoots (buds and bark):

*Dormant mature shoots*.—Color: Greyed-Red (RHS 178A) where exposed to full sunlight grading to Greyed-Orange (RHS 173B) with diminished light exposure. Texture: Very light pubescence which gradually disappears in older tissues. Size: 30-60 cm long; may have some spines.

*Axillary buds*.—Size: 2-3 mm long and 3 mm wide with little pubescence. Shape: Obtuse, sessile, somewhat appressed and flattened. Texture: Some pubescence.

*Bark on three-year-old shoots*.—Color: Greyed-Green (RHS 197A). Lenticels: Color: Greyed-Orange (RHS 163B). Size: 0.3-0.4 mm in diameter. Quantity: 1-2 lenticels per $cm^2$ Leaves:

*Mature leaves*.—Leaf arrangement: Alternate. Shape: Simple, recurved, oblong-ovate. Size: Length: 62 mm. Width: 50 mm at the widest point. Laminae: Somewhat wavy. Apex: Acuminate. Base: Nearly symmetrical rounded. Margin: Acutely serrated, with about 5 serrations per cm. Upper surface: Color: Green (RHS 127C). Texture: Glabrous and translucent. Lower surface: Color: Green (RHS 146C). Texture: Somewhat pubescent. Venation: Netted. Leaf poise: 15°-25° from the shoot, depending on shoot orientation. Stipules: Length: 8 mm. Width: 2 mm. Petioles: Diameter: 2 mm. Color: Gradation of Green (RHS 140A) to Greyed-Red (RHS 179A) depending on low or high exposure to light.

Flowers:

*Habit*.—Flowers borne on spurs, shoot terminals, and from lateral buds on growth from previous season.

*Flower diameter*.—40 mm.

*Fragrance*.—None.

*Buds*.—Location: Located on spurs and terminals; are mixed, typically producing a truss of 5 to 6 flowers and one bourse shoot. Shape: Lateral buds are obtuse, sessile and somewhat appressed. Size: Length: 4 mm. Width: 3 mm. Habit: Buds near the base of the shoot of the previous season usually produce 3 to 5 flowers and a single short shoot; mid-shoot buds may have 2-4 flowers; and more distal buds are usually vegetative.

*Petals*.—Size: Length: 25 mm. Width: 18 mm. Shape: Spatulate. Apex: Obtuse. Margin: Smooth. Texture: Smooth. Color: Closed petals: Red (RHS 54A). Open petals: White (RHS 155D) with Red (RHS 54A) striations in some of the petals.

*Reproductive organs*.—Pistils: Length: 6 mm. Color: Yellow-white (RHS 145B). Stamens: Length: 4 mm. Color: White (RHS 155D). Anther color: Yellow-Brown (RHS 167D).

Fruit:

*Mature fruit*.—Size: Height: 20-25 mm. Diameter: 25-30 mm. Shape: Obloid. Color: Partial Yellow-Orange skin (RHS 21C) with Red (RHS 41A) blush overtones depending on the exposure to the sun. Sepals: Persisting on a very protruding calyx. Flesh: Taste: Astringent (not meant for consumption). Color: Yellow-Orange (RHS 16A). Seed: Color: Greyed-Red (RHS 179A), translucent. Shape: Tear drop shape. Size: Length: 50-60 mm. Diameter: 25-35 mm at the widest point. Number: Generally five seed per fruit.

Disease resistance: As described above, the 'G.222' rootstock of the present invention exhibits resistance to fire blight. The percent lesion measured after inoculation of potted liners in the greenhouse using different strains of *E. amylovora* was negligible indicating resistance to the bacterium. Plants of 'G.222' are not infested by the woolly apple aphid *Eriosoma lanigerum*. The 'G.222' rootstock, having survived the inoculation with crown and root rot, is also considered resistant to crown and root rots caused by *Phytophthora cactorum*.

We claim:

1. A new and distinct variety of apple tree named 'G.222' herein described and illustrated.

* * * * *